United States Patent
Iikawa et al.

(10) Patent No.: US 8,733,150 B2
(45) Date of Patent: May 27, 2014

(54) COLUMN AND METHOD OF EVALUATION OF CONTAMINATED CONDITION OF GAS

(75) Inventors: Reiko Iikawa, Sodegaura (JP); Satoru Moriya, Sodegaura (JP); Kazuhiro Umehara, Osaka (JP); Ryota Nishioka, Osaka (JP)

(73) Assignee: Sumika Chemical Analysis Service, Ltd., Osaka-Shi (JP)

(*) Notice: Subject to any disclaimer, the term of this patent is extended or adjusted under 35 U.S.C. 154(b) by 406 days.

(21) Appl. No.: 13/127,746

(22) PCT Filed: Dec. 11, 2008

(86) PCT No.: PCT/JP2008/073027
§ 371 (c)(1),
(2), (4) Date: Jul. 19, 2011

(87) PCT Pub. No.: WO2010/067464
PCT Pub. Date: Jun. 17, 2010

(65) Prior Publication Data
US 2012/0017667 A1    Jan. 26, 2012

(51) Int. Cl.
G01N 30/02    (2006.01)
G01N 30/60    (2006.01)

(52) U.S. Cl.
USPC ......................................................... 73/23.39

(58) Field of Classification Search
USPC .......................................... 73/23.39; 96/101
See application file for complete search history.

(56) References Cited

U.S. PATENT DOCUMENTS

| | | | | |
|---|---|---|---|---|
| 4,066,677 A | * | 1/1978 | de Rosset et al. | 554/193 |
| 4,208,284 A | * | 6/1980 | Pretorius et al. | 210/767 |
| 4,366,060 A | * | 12/1982 | Leiser et al. | 210/635 |
| 4,732,887 A | * | 3/1988 | Obanawa et al. | 502/402 |
| 2010/0108608 A1 | * | 5/2010 | Cowieson | 210/660 |

FOREIGN PATENT DOCUMENTS

| JP | 11-90160 A | | 4/1999 |
|---|---|---|---|
| JP | 2003-222577 A | | 8/2003 |
| JP | 2008-185503 | * | 8/2008 |

OTHER PUBLICATIONS

Japan Air Cleaning Association, "Appendix 1: Measuring Method of Acidic Substance in Air of Cleanrooms and Associated Controlled Environments", JACA No. 35A-2003, Mar. 1, 2003, pp. 5-6.
Japan Air Cleaning Association, "Appendix 2: Measuring Method of Basic Substance in Air of Cleanrooms and Associated Controlled Environments", JACA No. 35A-2003, Mar. 1, 2003, pp. 7-9.
International Search Report, dated Mar. 31, 2009, issued in PCT/JP2008/073027.

* cited by examiner

*Primary Examiner* — Daniel S Larkin
(74) *Attorney, Agent, or Firm* — Birch, Stewart, Kolasch & Birch, LLP

(57) ABSTRACT

A gas adsorbing column filled with a filler composed of an adsorbent supported on a substrate having an average particle size or cross-sectional average diameter of 500 μm to 1000 μm, wherein the void volume of the column is 5 to 100 μl.

7 Claims, 2 Drawing Sheets

COLUMN AND METHOD OF EVALUATION OF CONTAMINATED CONDITION OF GAS

TECHNICAL FIELD

The present invention relates to a gas adsorbing column containing an acidic substance or basic substance, and a method of evaluation of the contaminated condition by an acidic substance or basic substance in a gas, using this column.

BACKGROUND ART

In an environment for producing an electronic board, such as a semiconductor wafer, liquid crystal board, magnetic disc and the like (hereinafter, referred to as board), contaminants, such as an acidic substance, basic substance and the like in its production space are adsorbed on a board to cause lowering of the yield of a product and reduction in its quality, thus, a step of producing such a board is carried out in a clean room. It is necessary to evaluate the contaminated condition by the above-described acidic substance, basic substance and the like in the clean room in each production process, and examples of the evaluation means include a method in which air in a clean room sucked by a suction pump is passed through an absorption solution at a constant flow rate to allow contaminants in the air to be absorbed, and the absorbed contaminants are analyzed, a method in which air in a clean room sucked by a suction pump is passed through a filter at a constant flow rate to allow contaminants in the air to be adsorbed, the contaminants are removed from the filter with a solvent, and the removed contaminants are analyzed, and the like (see, e.g., non-patent documents 1 and 2, patent document 1).

Recently, a clean room is required to ensure a more highly cleaned space, together with a need for a method of evaluating the contaminated condition by an acid or base with high sensitivity.

[Non-patent document 1] "Appendix 1: method of measuring acidic substance in clean room and associated controlled environment air", JACA No. 35A-2003: guideline of notation method and measurement method of air cleanliness relating to molecular contaminants in clean rooms and associated controlled environments, Japan Air Cleaning Association, 2003, March 1, p. 5-6

[Non-patent document 2] "Appendix 2: method of measuring basic substance in clean room and associated controlled environment air", JACA No. 35A-2003: guideline of notation method and measurement method of air cleanliness relating to molecular contaminants in clean rooms and associated controlled environments, Japan Air Cleaning Association, 2003, March 1, p. 7-9

[Patent document 1] JP-A No. 2003-222577

DISCLOSURE OF THE INVENTION

In the conventional methods of evaluation of the contaminated condition of gas, an absorption solution is concentrated and analyzed in the case of the low concentration of contaminants in air or atmosphere, however, it is difficult to subject the concentrated solution to whole quantity analysis, namely, to subject contaminants absorbed in the absorption solution to whole quantity analysis, meaning that these evaluation methods are not sufficiently satisfactory from the standpoint of evaluation with high sensitivity. Further, in the evaluation methods using an absorption solution, there is a possibility of contamination of a clean room with the absorption solution.

Under such a situation, it has been investigated for responding to the above-described problems and resultantly found that if contaminants such as an acidic substance, basic substance and the like in a gas are adsorbed using a certain kind of column and the contaminants adsorbed on the column are extracted with a solvent under an online condition and analyzed, then, the contaminated condition can be evaluated simply and with good precision without using an absorption solution in sampling contaminants in air or atmosphere.

That is, the present invention provides the following [1] to [7].

[1] A gas adsorbing column filled with a filler composed of an adsorbent supported on a substrate having an average particle size or cross-sectional average diameter of 500 μm to 1000 μm, wherein the void volume of the column is 5 to 100 μl.

[2] The column according to [1], wherein the adsorbent is a basic substance.

[3] The column according to [2], wherein the basic substance is at least one compound selected from the group consisting of alkali metal carbonates, alkali metal hydroxides, amines and ammonium compounds.

[4] The column according to [1], wherein the adsorbent is an acidic substance.

[5] A method of evaluating the contaminated condition of a gas in which a gas as an evaluation subject is ventilated into the column according to [1], thereby allowing an acidic substance or basic substance contained in the gas to be adsorbed on the filler in the column, and the adsorbed acidic substance or basic substance is extracted with a solvent under an online condition and analyzed.

[6] A method of evaluating the contaminated condition of a gas in which a gas as an evaluation subject is ventilated into the column according to [2] or [3], thereby allowing an acidic substance contained in the gas to be adsorbed on the filler in the column, and the adsorbed acidic substance is extracted with a solvent under an online condition and analyzed.

[7] A method of evaluating the contaminated condition of a gas in which a gas as an evaluation subject is ventilated into the column according to [4], thereby allowing a basic substance contained in the gas to be adsorbed on the filler in the column, and the adsorbed basic substance is extracted with a solvent under an online condition and analyzed.

Figure 1:
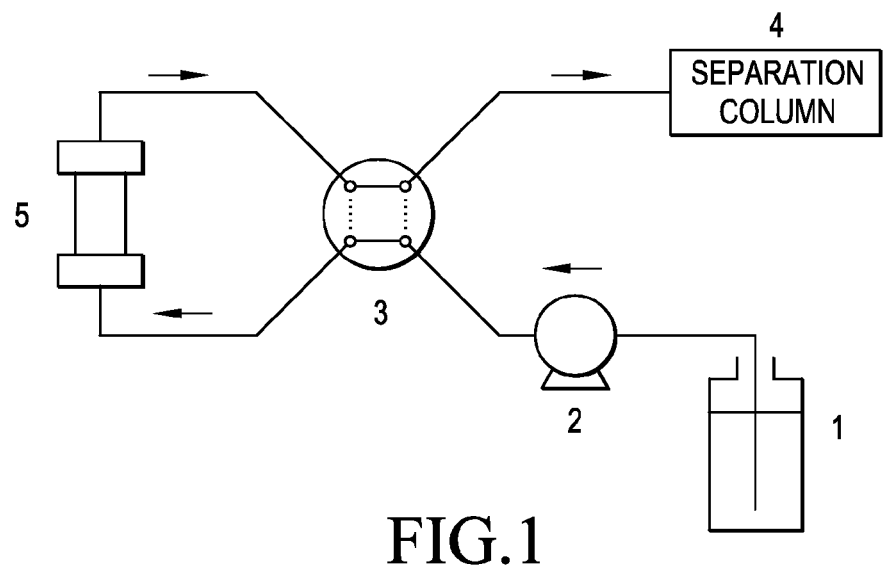
FIG. 1 is a schematic view of an apparatus used in performing extraction with a solvent under an online condition and analyzing the extraction solution.

| [Description of marks] | |
| --- | --- |
| 1: | eluent |
| 2: | pump |
| 3: | 4-way valve |
| 4: | separation column |
| 5: | gas adsorbing column |

MODES FOR CARRYING OUT THE INVENTION

The column of the present invention is a column filled with a filler composed of an adsorbent supported on a substrate.

The material of the substrate includes glass, quartz, polycarbonate resin, polystyrene resin, polyamide resin and the like. Preferably, the substrate is glass or quartz.

The shape of the substrate is preferably a shape having large surface area, and includes a granular shape, fibrous shape and the like. Preferably, the shape is a granular shape.

The average particle size of the substrate or the cross-sectional average diameter of the substrate is preferably 500 µm or more, more preferably 600 µm or more from the standpoint of enhancement of ventilation efficiency. From the standpoint of enhancement of collection efficiency, it is preferably 1000 µm or less, more preferably 850 µm or less. In this case, the measurement method is carried out according to JIS K0069 "Test Methods for Sieving of Chemical Products".

As the adsorbent, use is made of basic substances or acidic substances.

The basic substance to be used as the adsorbent includes inorganic bases and organic bases. The inorganic base includes alkali metal carbonates, alkali metal hydroxides and the like, and the organic base includes amines, ammonium compounds and the like.

The basic substance to be used as the adsorbent is preferably at least one compound selected from the group consisting of alkali metal carbonates, alkali metal hydroxides, amines and ammonium compounds.

The alkali metal carbonate includes sodium carbonate, potassium carbonate, potassium hydrogen carbonate and the like. The alkali metal hydroxide includes strontium hydroxide, potassium hydroxide, sodium hydroxide and the like. The amine includes triethanolamine and the like. The ammonium compound includes tetramethylammonium hydroxide, tetrabutylammonium hydroxide and the like.

The basic substance to be used as the adsorbent is more preferably at least one compound selected from the group consisting of sodium carbonate, sodium hydroxide and triethanolamine.

The acidic substance to be used as the adsorbent includes inorganic acids and organic acids.

The inorganic acid includes sulfuric acid, phosphoric acid and the like. The organic acid includes methanesulfonic acid, maleic acid, malonic acid and the like.

The acidic substance to be used as the adsorbent is preferably at least one compound selected from the group consisting of sulfuric acid, phosphoric acid and methanesulfonic acid.

The method of allowing the adsorbent to be supported on a substrate includes, when the adsorbent is a solid substance, a method in which the solid substance is dissolved in a solvent to prepare a solution and the solution is coated on a substrate, or a substrate is immersed in the solution and the solvent is dried, and when the adsorbent is a liquid substance, a method in which the liquid substance is coated as it is on a substrate or the liquid substance is dissolved in a solvent to prepare a solution and the solution is coated on a substrate, or a substrate is immersed in the solution and the solvent is dried, and the like.

Further, a moisturizing agent may also be coated on a substrate, in addition to the adsorbent. Exemplified as the moisturizing agent are polyhydric alcohols, such as ethylene glycol, propylene glycol, glycerin and the like; polyalkylene glycols, such as polyethylene glycol, polypropylene glycol and the like.

It is preferable for the column to be made of a material exerting no influence on analysis of an acidic substance or basic substance as an analysis subject and to have pressure resistance enduring a pressure of about 10 Mpa. As the material of the column, stainless, polyether ether ketone resins and the like are usually used. As the column, those having a cylindrical shape are usually used, and preferably are columns composed of a column body, frit, sleeve and end fitting, and examples thereof include those described in JP-A No. 2001-249120.

Regarding the volume of the column, those having a suitable size corresponding to the analysis treatment amount can be used. The column volume is usually 0.1 ml to 5 ml, preferably 0.2 ml to 3 ml.

The void volume of the column after filling with a filler is 5 µl to 100 µl, and when the void volume is too small, the ventilating rate of a gas into the column lowers, and in the case of performing ventilation by a suction pump, load on the suction pump increases, in some cases. When the void volume is too large, a separation column of a measurement apparatus is dried and deteriorated by bubbles exiting from the column in extraction under an online condition, in some cases. The void volume of the column is preferably 10 µl to 50 µl. The void volume does not include the volume of a portion for connecting a piping, for example, in the case of a column consisting of a column body, frit, sleeve and end fitting, it does not include the volume of an internal thread part provided on an end fitting or column body for connecting to a piping.

In evaluating the amount of an acidic substance or basic substance in a gas as an evaluation subject in the evaluation method of the present invention, a gas as an evaluation subject is ventilated into a column, and the acidic substance or basic substance contained in the gas as an evaluation subject is adsorbed on a filler in the column. Ventilation is carried out usually using a suction pump. The ventilation rate is preferably 0.1 to 2 L/min. The ventilation time is preferably several minutes to 24 hours.

Ventilation of a gas as an evaluation subject into a column is usually carried out in a space as an evaluation subject, such as a clean room, clean booth and the like. In transportation of a column, an orifice part of the column is sealed with a plug not contaminated with an analysis subject substance, and/or, the column is accommodated in a sealed vessel not contaminated with an analysis subject substance.

The column after ventilated by a gas as an evaluation subject is connected to a measurement apparatus and extracted with a solvent under an online condition to cause extraction of contaminants from a filler, and the extracted solution is subjected to whole amount analysis and the contaminated condition of the gas is evaluated. Here, "extracted with a solvent under an online condition" means an embodiment in which a column after ventilated by a gas as an evaluation subject and an analysis column are connected in series in an identical line, for example, between a pump for feeding an extraction solution to an analysis column and an analysis column, a column after ventilated by a gas as an evaluation subject is connected, and under this constitution, an extraction solution flows into the column, and an extraction solution containing contaminants extracted by the extraction solution is introduced into the analysis column.

Analysis of the extraction solution is carried out usually by a liquid chromatograph method, and examples thereof include an anion exchange method and cation exchange method using an ion exchange column, an ion chromatograph method of suppressor mode using a suppressor, a reverse phase chromatograph method using an ODS column, and the like.

Figure 2:
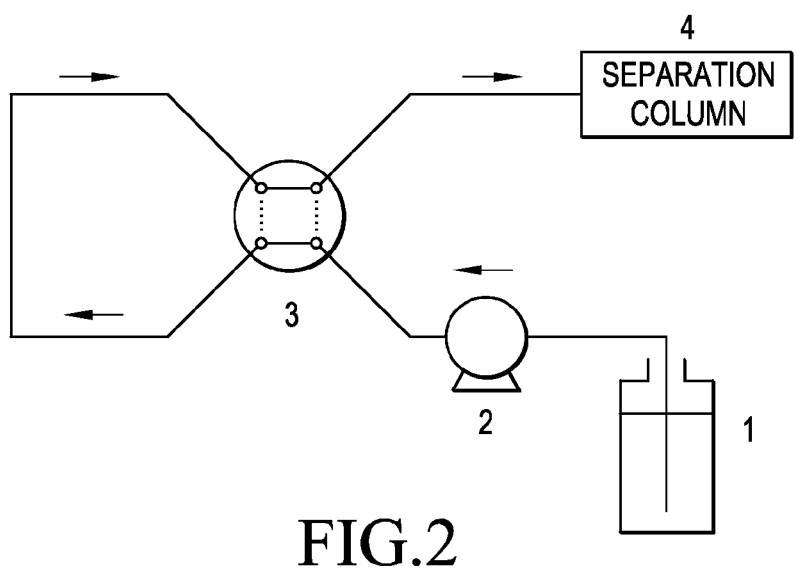
FIG. 2 is a schematic view of an apparatus in which a gas adsorbing column is not connected.
Figure 3:
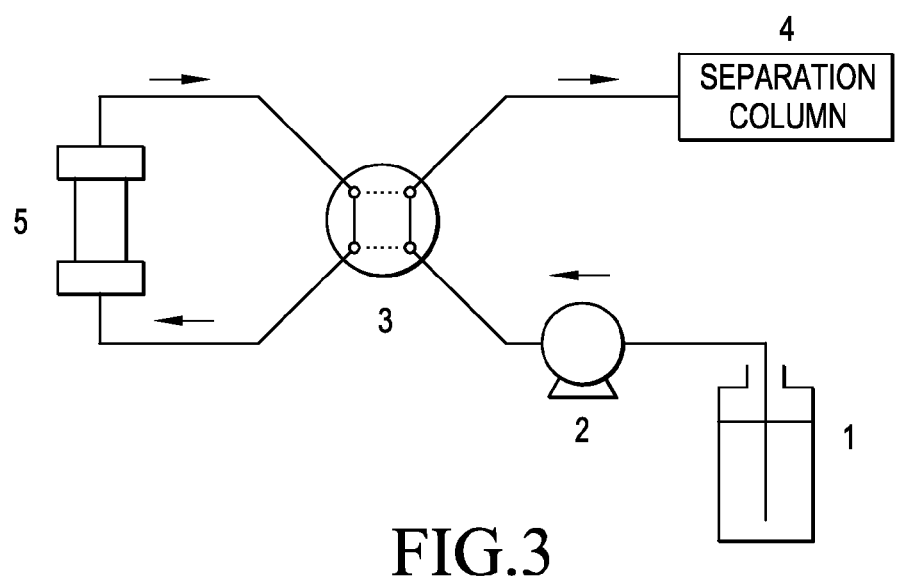
FIG. 3 is a schematic view of an apparatus in which a gas adsorbing column is connected to an analysis apparatus.

As an apparatus for performing extraction with a solvent under an online condition and feeding the whole amount of an extraction solution to a measurement apparatus, there is an apparatus having a constitution as shown in FIG. 1 having a feeding pump and a 4-way valve. The apparatus in which a gas adsorbing column is not connected has a constitution as shown in FIG. 2. From this constitution of FIG. 2, the 4-way valve is switched and a gas adsorbing column is connected to the apparatus, to obtain a constitution as shown in FIG. 3. In measurement, the 4-way valve is switched to obtain a constitution as shown in FIG. 1.

The acidic substance as an analysis subject substance includes acids themselves, such as hydrogen chloride, nitric acid, sulfuric acid, phosphoric acid, hydrofluoric acid, formic acid, acetic acid and the like, and additionally, ammonium fluoride, ammonium formate, ammonium acetate and the like. The basic substance as an analysis subject substance includes bases themselves, such as ammonia, trimethylamine, triethylamine, alkanolamine and the like, an additionally, ammonium fluoride, ammonium formate, ammonium acetate and the like.

The space as an evaluation subject includes a clean room and clean booth. Also mentioned are EFEM (Equipment Front End Module), FOUP (Front Opening Unified Pod), SMIF (Standard Mechanical Interface) pod and the like defined in the SEMI (Semiconductor Equipment and Materials International) standard.

According to the present invention, the contaminated condition of a gas by an acidic substance or basic substance can be evaluated with high sensitivity, and can be evaluated without using an absorption solution.

EXAMPLES

The present invention will be illustrated further in detail by examples.

Example 1

Preparation of Gas Adsorbing Column

A granular quartz sand having a particle size of 600 to 850 μm was filled in a stainless column having an inner volume of 0.27 ml, and ultrapure water was passed into the column to wash the inside of the column. Next, a mixed aqueous solution containing sulfuric acid and glycerin was passed into the column, and nitrogen was ventilated to dry the solvent, to prepare a gas adsorbing column. This gas adsorbing column had a void volume of 45 μl.
(Evaluation of Contaminated Condition of Laboratory)

To the gas adsorbing column was connected a gas suction pump, and air in a laboratory was ventilated into the gas adsorbing column at a suction rate of 0.5 L/min for one hour. Next, the gas adsorbing column was connected to an ion chromatograph, and ammonium adsorbed on the adsorbent in the gas adsorbing column was extracted with a solvent under an online condition, and the adhesion amount of an ammonium ion was measured by the ion chromatograph. The analysis results are shown in Table 1.

Example 2

Evaluation of Contaminated Condition of Clean Booth

To a gas adsorbing column prepared in the same manner as in Example 1 was connected a gas suction pump, and air in a clean booth placed in a laboratory was ventilated into the gas adsorbing column at a suction rate of 0.5 L/min for 24 hours. Next, the gas adsorbing column was connected to an ion chromatograph, and ammonium adsorbed on the adsorbent in the gas adsorbing column was extracted with a solvent under an online condition, and the adhesion amount of an ammonium ion was measured by the ion chromatograph. The analysis results are shown in Table 1.

TABLE 1

| | Ammonium ion concentration ($\mu g/m^3$) |
|---|---|
| Laboratory | 1.4 |
| Clean booth | 0.21 |

The invention claimed is:

1. A gas adsorbing column filled with a filler composed of an adsorbent supported on a substrate having an average particle size or cross-sectional average diameter of 500 μm to 1000 μm, wherein the void volume of the column is 5 to 100 μl.

2. The column according to claim 1, wherein the adsorbent is a basic substance.

3. The column according to claim 2, wherein the basic substance is at least one compound selected from the group consisting of alkali metal carbonates, alkali metal hydroxides, amines and ammonium compounds.

4. The column according to claim 1, wherein the adsorbent is an acidic substance.

5. A method of evaluating a contaminated condition of a gas in which a gas as an evaluation subject is ventilated into the column according to claim 4, thereby allowing a basic substance contained in the gas to be adsorbed on the filler in the column, and the adsorbed basic substance is extracted with a solvent under an online condition and analyzed.

6. A method of evaluating a contaminated condition of a gas in which a gas as an evaluation subject is ventilated into the column according to claim 1, thereby allowing an acidic substance or basic substance contained in the gas to be adsorbed on the filler in the column, and the adsorbed acidic substance or basic substance is extracted with a solvent under an online condition and analyzed.

7. A method of evaluating a contaminated condition of a gas in which a gas as an evaluation subject is ventilated into the column according to claim 2 or 3, thereby allowing an acidic substance contained in the gas to be adsorbed on the filler in the column, and the adsorbed acidic substance is extracted with a solvent under an online condition and analyzed.

* * * * *